United States Patent
Miller

(10) Patent No.: US 11,367,522 B2
(45) Date of Patent: Jun. 21, 2022

(54) MEDICAL IMAGE DISPLAY METHOD AND APPARATUS

(71) Applicant: CANON MEDICAL SYSTEMS CORPORATION, Otawara (JP)

(72) Inventor: David Innes Miller, Edinburgh (GB)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 74 days.

(21) Appl. No.: 16/830,930

(22) Filed: Mar. 26, 2020

(65) Prior Publication Data
US 2021/0304873 A1 Sep. 30, 2021

(51) Int. Cl.
G16H 30/20 (2018.01)
G16H 30/40 (2018.01)
G06T 7/00 (2017.01)

(52) U.S. Cl.
CPC ........... *G16H 30/20* (2018.01); *G06T 7/0012* (2013.01); *G16H 30/40* (2018.01); *G06T 2207/10081* (2013.01)

(58) Field of Classification Search
CPC ...... G16H 30/20; G16H 30/40; G06T 7/0012; G06T 2207/10081; H04L 67/22; H04L 67/306
See application file for complete search history.

(56) References Cited

U.S. PATENT DOCUMENTS

| | | | |
|---|---|---|---|
| 9,703,451 B2 * | 7/2017 | Barger | G06F 3/04817 |
| 2007/0115282 A1 | 5/2007 | Turner et al. | |
| 2009/0129643 A1 | 5/2009 | Natanzon et al. | |
| 2010/0063842 A1 * | 3/2010 | Carroll | A61B 6/463 705/3 |
| 2013/0266242 A1 * | 10/2013 | Dorn | G06T 1/60 382/305 |
| 2014/0278195 A1 | 9/2014 | Feiweier et al. | |
| 2015/0356245 A1 * | 12/2015 | Kozuka | G06F 3/0488 705/2 |
| 2018/0292963 A1 * | 10/2018 | Nanjo | G06T 7/0012 |
| 2020/0321098 A1 * | 10/2020 | Saptharishi | G16H 30/40 |

FOREIGN PATENT DOCUMENTS

JP WO2009063900 A1 * 3/2011 ............ G16H 30/40

* cited by examiner

*Primary Examiner* — Vu Le
*Assistant Examiner* — Julius Chai
(74) *Attorney, Agent, or Firm* — Oblon, McClelland, Maier & Neustadt, L.L.P.

(57) ABSTRACT

A medical system comprises processing circuitry configured to: load medical images sequentially from a data store which stores a set of medical images, each having an associated location; receive a current location of a medical image that is currently displayed on the display; receive an input operation from a user; process the input operation to determine whether the input operation is of a first type or the input operation is of a second type, wherein the first type of input operation is intended to be less precise than the second type of input operation, and to determine a destination location in dependence on the current location and the input operation; perform a first display operation based on the destination location if the input operation is of the first type; and perform a second display operation based on the destination location if the input operation is of the second type.

18 Claims, 7 Drawing Sheets

MEDICAL IMAGE DISPLAY METHOD AND APPARATUS

FIELD

Embodiments described herein relate generally to a method and apparatus for displaying medical images, for example for displaying images in a series as a user navigates through the series.

BACKGROUND

It is known to store medical images using the DICOM (Digital Imaging and COmmunications in Medicine) standard. Images may be stored on a disk to be loaded into memory, and then loaded into memory on demand. For example, the disk may be a remote disk that is accessible via a network. If a user requests to view an individual image, the image may be loaded from the disk into memory in response to the user request.

A medical scanning procedure may result in a large quantity of DICOM images. Data from a volumetric scan such as a computed tomography (CT) scan may be processed to obtain slice images, where each slice image is representative of a slice through a subject's anatomy. In some circumstances, the entire body of a subject may be imaged at high resolution, for example using 1 mm slices. The number of slices obtained from a scan may therefore may be very large, for example in the hundreds or thousands. In many cases, a user (for example, a clinician) viewing the images obtained from the scan may only be interested in a small subset of the images. For example, the user may only be interested in one anatomical region.

In the below description, references to loading DICOM images into memory are taken to refer to the process of taking unprocessed DICOM data into memory, and turning the unprocessed DICOM data into unprocessed pixel data plus parsed DICOM metadata. Loading DICOM images uses system resources, for example, CPU (central processing unit), RAM (random access memory), Network and Disk I/O (Input/Output) resources. In particular, the parsing of the DICOM metadata uses a significant amount of CPU resource.

Images may be viewed in a 2D viewing system. The 2D viewing system may support viewing of images by multiple users. In a 2D viewing system that aims to support a very large number of users, system resources may be scarce.

Images may be stored in a central location and loaded over a network. Loading DICOM images over a network typically takes time. If the network has a high latency and/or low bandwidth, then loading may take even longer.

Typically, a user would prefer to see images immediately. The user would also like to be able to scroll through a series of images at a high rate of frames per second. For example, the user may want to be able to scroll through all of the slices obtained from a scan of a subject at a high speed.

One option is to load all of the images in a DICOM series when the DICOM series is requested. However, a clinician or other user may not look at all of the images in a DICOM series. If the clinician does not look at all the images then the loading of the DICOM images that were not viewed may be seen as a waste of system resources. The use of system resources to load images that are not viewed may impact the number of users that a given system can support.

Another option is to load individual DICOM images on demand. However, fetching and parsing a DICOM image on demand may not happen quickly enough to give a user an experience that they are looking for. This may impact the user's satisfaction with the system.

BRIEF DESCRIPTION OF THE DRAWINGS

Embodiments are now described, by way of non-limiting example, and are illustrated in the following figures, in which.

DETAILED DESCRIPTION

Certain embodiments provide a medical system comprising processing circuitry configured to: load medical images sequentially from a data store which stores a set of medical images, each of the set of medical images having an associated location; receive a current location of a medical image that is currently displayed on the display; receive an input operation from a user; process the input operation to determine whether the input operation is of a first type or the input operation is of a second type, wherein the first type of input operation is intended to be less precise than the second type of input operation, and to determine a destination location in dependence on the current location and the input operation; perform a first display operation based on the destination location if the input operation is of the first type; and perform a second display operation based on the destination location if the input operation is of the second type.

Certain embodiments provide a method comprising: loading medical images sequentially from a data store which stores a set of medical images, each of the set of medical images having an associated location; receiving a current location of a medical image that is currently displayed on the display; receiving an input operation from a user; processing the input operation to determine whether the input operation is of a first type or the input operation is of a second type, wherein the first type of input operation is intended to be less precise than the second type of input operation, and to determine a destination location in dependence on the current location and the input operation; performing a first display operation based on the destination location if the input operation is of the first type; and performing a second display operation based on the destination location if the input operation is of the second type.

Figure 1:
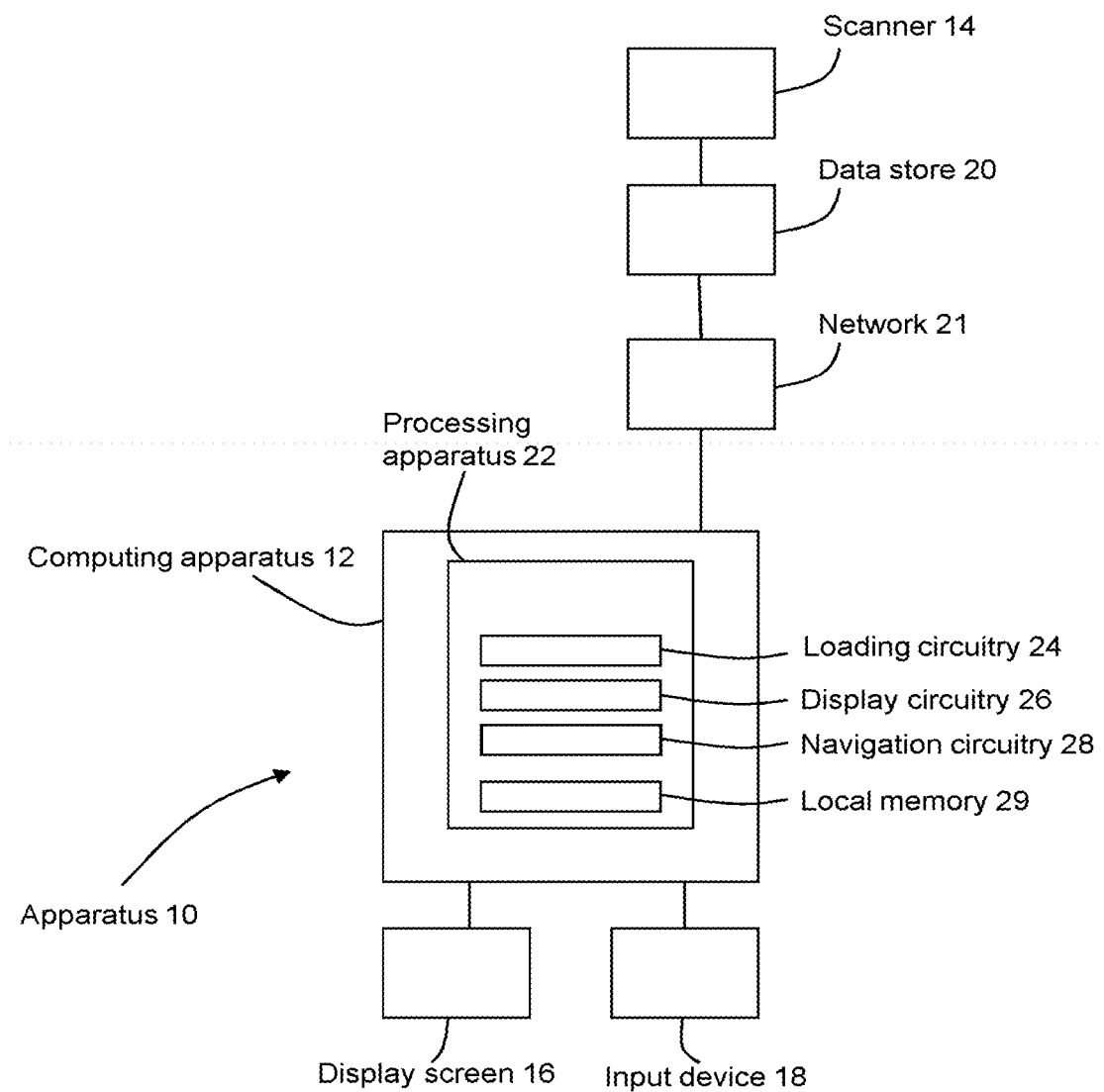
FIG. 1 is a schematic diagram of a medical system according to an embodiment.

A medical system 10 according to an embodiment is illustrated schematically in FIG. 1. The medical system 10 comprises a computing apparatus 12, in this case a personal computer (PC) or workstation. The computing apparatus 12 is connected to one or more display screens 16 and an input device or devices 18, such as a computer keyboard, mouse or trackball.

The computing apparatus 12 is configured to load image data sets from a data store 20 over a network 21.

In the present embodiment, the scanner 14 is a computed tomography (CT) scanner that is configured to acquire volumetric imaging data by scanning at least part of a patient or other subject. In other embodiments, the scanner 14 may comprise any scanner that is configured to perform medical imaging. The scanner 14 is configured to generate medical imaging data, which may comprise two-, three- or four-dimensional data in any imaging modality. For example, the scanner 14 may comprise a magnetic resonance (MR or MRI) scanner, CT (computed tomography) scanner, cone-beam CT scanner, X-ray scanner, ultrasound scanner, PET (positron emission tomography) scanner or SPECT (single photon emission computed tomography) scanner.

Imaging data acquired by the scanner 14 in a medical imaging procedure is processed to obtain a plurality of image data sets. In the present embodiment, the volumetric CT imaging data obtained by the CT scanner 14 is processed by processing circuitry (not shown) of the CT scanner 14 to obtain a plurality of slice image data sets, each of which is representative of a respective slice of a scanned volume. Each of the slice image data sets is associated with a respective location. Typically, the slices are axial slices, and the locations of the slice image data sets are distributed along a longitudinal axis of the patient or other subject. Image data sets obtained from the scanner 14 are stored in the data store 20.

In other embodiments, the image data sets may have been obtained by processing data acquired by any suitable scanner or scanners.

Image data sets may also be stored in one or more further data stores (not shown) which may form part of a Picture Archiving and Communication System (PACS). The data store 20 or any further data store may comprise any suitable form of data storage. The computing apparatus 12 may be configured to load image data sets from a further data store over the network 21 or over a further network (not shown).

Computing apparatus 12 comprises a processing apparatus 22 for processing of data, including image data. The processing apparatus comprises a central processing unit (CPU) and Graphical Processing Unit (GPU). In other embodiments, the processing apparatus may comprise a CPU without a GPU.

The processing apparatus 22 includes a local memory 29 configured to store image data sets locally.

The processing apparatus 22 includes loading circuitry 24 configured to load image data from data store 20 into the local memory 29, display circuitry 26 configured to display images on display screen 16 and navigation circuitry 28 configured to navigate through image data sets, for example slices.

In the present embodiment, the circuitries 24, 26, 28 are each implemented in the CPU and/or GPU by means of a computer program having computer-readable instructions that are executable to perform the method of the embodiment. In other embodiments, the various circuitries may be implemented as one or more ASICs (application specific integrated circuits) or FPGAs (field programmable gate arrays).

The computing apparatus 12 also includes a hard drive and other components of a PC including RAM, ROM, a data bus, an operating system including various device drivers, and hardware devices including a graphics card. Such components are not shown in FIG. 1 for clarity.

As described above, the computing apparatus 12 and in particular the loading circuitry 24 are configured to load image data sets from the data store 20 into the local memory 29. In the discussion below, we refer to the loading of images. A reference to loading an image is intended to refer to loading the image data set associated with that image. To load the image, the loading circuitry 24 requests that the image data set be transmitted from the data store 20. The data store 20 transmits the image data set across the network 21 to the computing apparatus 12. When received by the computing apparatus 12, the image data set comprises unprocessed DICOM data. The loading circuitry 24 converts the unprocessed DICOM data into unprocessed pixel data and parsed DICOM metadata. The unprocessed pixel data and parsed DICOM metadata is stored locally at the computing apparatus 12 in local memory 29. A reference to loading an image does not necessarily imply that the image is displayed.

Figure 2:
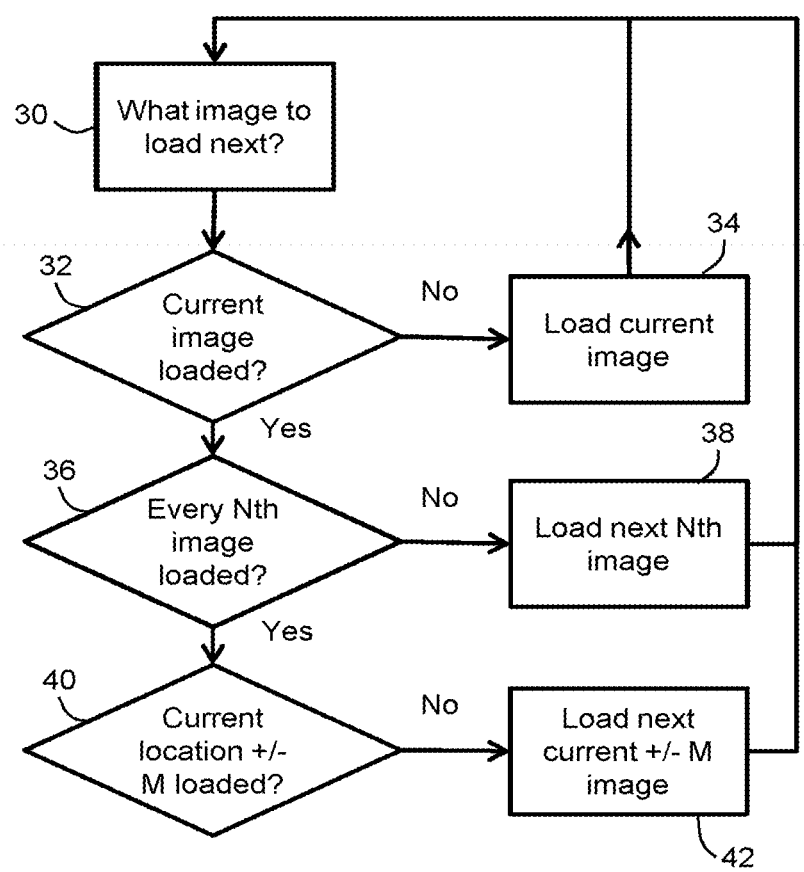
FIG. 2 is a flowchart illustrating a predetermined loading rule in accordance with an embodiment.

FIG. 2 is a flow chart illustrating in overview a predetermined loading rule in accordance with an embodiment. As described above, it would be possible to load all images associated with a given scan (for example, to load all images in order) but this could take up substantial resources if there are a large number of images. Alternatively, a choice could be made to load few or no images initially, but this could result in a poor experience for a user if the user has to wait for each image to load before it is displayed. Therefore, in the present embodiment, a predetermined loading rule is used to load images in an order that is anticipated to be useful to a user, without consuming excessive resources.

In the embodiment of FIG. 2, the images to be loaded are axial slices obtained from a CT scan. Each image is associated with a respective location. The locations are positions along a longitudinal axis of the subject that was scanned. For example, the locations may be longitudinal positions in millimeters. The loading and display of images starts with an initial image at an initial location. In the present embodiment, the initial image is a slice at the very top of the subject's head. The initial image may also be referred to as the 1st image. In other embodiments, a different location may be used for the initial image. For example, the location of the initial image may be set to be a location of interest, for example a location of a finding or of an anatomical landmark.

The user may be any person who is authorized to view the medical images, for example a clinician, a radiologist, a radiographer, or a researcher.

The user may navigate through the axial slices by providing an input that is representative of a location along the longitudinal axis, or of a change in location along the longitudinal axis. Specific input methods are described below with reference to FIG. 3. The navigation circuitry 28 may change a current location on the longitudinal axis in response to the user's input.

The predetermined loading rule of FIG. 2 starts when no image has yet been loaded. For simplicity, we first describe the case in which no user input is received while images are being loaded in accordance with the predetermined loading rule. In this case, the current location within the set of slices starts as the location of the initial image, and does not change while images are loaded in accordance with the predetermined loading rule. We then describe the case in which the current location changes while images are being loaded in accordance with the predetermined loading rule.

At stage 30 of FIG. 2, the loading circuitry 24 asks a question of which image to load next. The loading circuitry 24 proceeds to a stage 32 at which it asks whether the current image is loaded. The current image is the image at the current location. We consider the case in which the current location is the location of the initial image, and in which the initial image is at the top of the subject's head. In other circumstances, the current location may be at any appropriate location along the longitudinal axis.

At the first instance of stage 32, the answer to whether the current image is loaded is no. No image has yet been loaded. The loading circuitry 24 proceeds to stage 34. At stage 34, the loading circuitry 24 requests loading of the current image, which is the initial image. The data store 20 transmits the image data set for the initial image to the computing apparatus 12. The loading circuitry 24 loads the initial image into local memory 29.

The display circuitry 26 displays the initial image on the display screen 16 once the initial image has been loaded.

The flow chart of FIG. 2 returns to stage 30 and then to stage 32. If no user input has been received to change the current location, the current image is still the initial image, which has now been loaded. At stage 32, the loading circuitry 24 determines that the current image has been loaded and proceeds to stage 36. At stage 36, the loading circuitry 24 asks whether every Nth image has been loaded.

A feature of the loading rule of FIG. 2 is that it loads a subset of the images associated with the scan before loading further images. The subset comprises every Nth image. The subset of images may also be referred to as a grid of images. The locations of each image in the subset of images may be described as candidate locations.

In the present embodiment, N=10. The subset of images comprises every 10th image. In other embodiments, N may take any appropriate value. For example, the subset may comprise every 5th, 15th, or 20th image. In some embodiment, a value for N is set on installation. In some embodiments, a value for N is selected by a user. A value for N may be tuned to a user's preference, for example based on past inputs from the user. A value for N may be selected based on system considerations, for example based on resource availability. If resource availability is good, a low value of N may be chosen. If resource availability is poor, a higher version of N may be chosen. In some circumstances, different values for N may be applied to different users.

Since none of the subset have yet been loaded, the loading circuitry 24 proceeds to stage 38. The loading circuitry 24 requests the next Nth image, which in a first iteration of stage 38 is the 11th image. The data store 20 transmits the 11th image to the computing apparatus 12. The loading circuitry 24 loads the next Nth image into the local memory 29.

Once the next Nth image has been loaded, the flow chart returns to stages 30 and 32. In the absence of user input, the initial image is still the current image. The current image has already been loaded.

The loading circuitry 24 proceeds to stage 36 and there are still Nth images to be loaded. The loading circuitry 24 proceeds to stage 38 and loads the next Nth image, which is the 21st image. In the case in which no user input has been received to change the current location, the flow chart repeats from stages 30 to 38 until all of the subset of Nth images has been loaded.

Once all of the Nth images have been loaded, the loading circuitry 24 proceeds from stage 36 to stage 40. At stage 40, the loading circuitry 24 asks whether the images close to the current location have been loaded. In the present embodiment, images are considered close to the current location if they are within M images of the current location. For example, M may be 5.

If there are images within M images from the current location that have not been loaded, the loading circuitry 24 proceeds to stage 42. The loading circuitry 24 loads an image within M images of the current image that has not yet been loaded. For example, in the case in which the current location is still the initial location, and no images between the 1st image and the 10th image have yet been loaded, the loading circuitry 24 requests transmission of the 2nd image. The data store 20 transmits the 2nd image to the computing apparatus 20. The loading circuitry 24 loads the 2nd image into the local memory 29. The loading circuitry 24 repeats stages 30 to 42 until images within M images of the current image have been loaded. In the case of the initial image, the images within 5 images are the 2nd to 6th images.

An instance of the predetermined loading rule is completed when the current image, Nth images, and closest M images to the current image have all been loaded. It may be seen that the predetermined loading rule does not load all of the images.

In the description of FIG. 2 above, the current location does not change during loading, so the initial image is the current image throughout. In other embodiments, the current location may change during loading.

If a current location changes while the images are loading in accordance with the predetermined loading rule, the predetermined loading rule may be halted or altered in response to the change in current location. A set of images to be loaded may be queued. In some circumstances, the queue may be altered or abandoned in response to a change in current location.

The current location may change at various different points within the predetermined loading rule. In a first example, the current location changes during the loading of the initial image. In a first instance of stage 30, the loading circuitry 24 asks which image to load. At stage 32, the loading circuitry 24 asks whether the current image is loaded. Initially, no image has been loaded. The loading circuitry proceeds to stage 34 and loads the initial image. The current location is changed during or immediately after the loading of the initial image. The loading circuitry 24 performs a second instance of stages 30 and 32. At the second instance of stage 32, the loading circuitry 24 asks whether the image at the current location has been loaded. The change in current location results in the current location being a location that has not yet been loaded. The loading circuitry 24 proceeds to stage 34 and loads the image at the current location.

In a second example, the current location changes during the loading of the Nth images. For example, consider a case in which N is 10, and in which the current location changes after loading the 11th image. After loading the 11th image, the loading circuitry 24 proceeds to stages 30 and 32. At stage 32, the loading circuitry 24 asks whether the image at the current location has been loaded. If the current location has changed to a location of an image that has already been loaded, the loading circuitry 24 proceeds to stage 36 and continues to load Nth images as described above, starting with the 21st image. If the current location has changed to a location of an image that has not been loaded, the loading circuitry 24 proceeds to stage 34 and loads the image at the current location. The loading circuitry then proceeds to stages 30 and 32. If the current location has not changed again, the loading circuitry proceeds to stage 36 and continues to load Nth images as described above, starting with the 21st image.

In a third example, the current location changes during the loading of the images within M images from the current location. For example, consider a case in which the loading of the initial, 1st image is followed by loading of all of the Nth images, while the current location remains at the initial location. At a first instance of stage 42, the loading circuitry 24 loads the 2nd image. The current location then changes to, for example, the location of the 17th image. The loading circuitry 24 proceeds to stages 30 and 32. At stage 32, the loading circuitry 24 determines that the 17th image has not yet been loaded. At stage 34, the loading circuitry 24 loads the 17th image. The loading circuitry 24 proceeds to stages 30 and 32, and at stage 32 determines that the 17th image has now been loaded. The loading circuitry 24 proceeds to stage 36, at which it determines that every Nth image has been loaded. The loading circuitry 24 proceeds to stage 40, at which it determines that some the M images before and after the 17th image have not yet been loaded. At stage 42, the loading circuitry 24 loads the 18th image. If no further change is made to the current location, the loading circuitry 24 repeats stages 30, 32, 36, 40 and 42 until the 19th, 20th and 22nd images are loaded (the 21st image having previously been loaded as part of the Nth images), and the 12th to 16th images are loaded.

In this third example, the loading circuitry 24 repeats stages 30, 32, 36, 40 and 42 until images within M images of the current image in a positive direction and images within M images of the current image in a negative direction have been loaded. In other embodiments, the loading circuitry 24 may load M images in a selected direction and not in the other direction. For example, the loading circuitry 24 may load M images in a current direction of scrolling.

In the method of FIG. 2, the current image is loaded; followed by the subset of Nth images; followed by the M images that are closest to the current image. In other embodiments, a different order of loading may be used. For example, the M closest images may be loaded before the subset of Nth images.

In other embodiments, the predetermined loading rule may load images based on further criteria. The predetermined loading rule may comprise loading images for locations that match locations from one or more captured findings, for example the location of one or more tumors. The predetermined loading rule may comprise loading images for locations for one or more anatomical landmarks, for example for a set of detected and diagnostically useful anatomical landmarks. The landmarks may be selected based on a pathology that is present in the medical images, or that the scan has been obtained in order to diagnose. The loading circuitry 24 may determine the pathology based on clinical codes or on a series description, or using any suitable method.

The images corresponding to findings and/or landmarks may be loaded in any suitable order relative to the other components of the predetermined loading rule. For example, the images corresponding to findings and/or landmarks may be loaded before or after the closest M images. The images corresponding to findings and/or landmarks may be loaded before or after the subset of Nth images.

Figure 3:
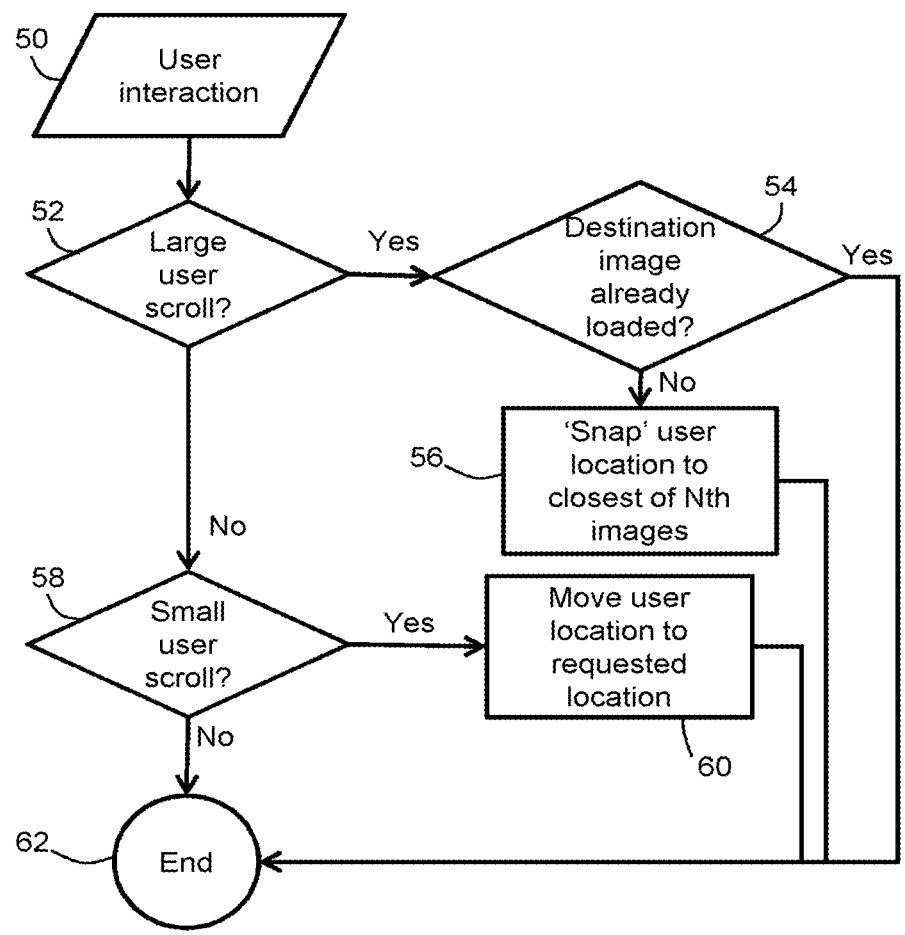
FIG. 3 is a flowchart illustrating a navigation method in accordance with an embodiment.

FIG. 3 is a flow chart illustrating in overview a method of navigating through the set of slices based on an input operation from a user. At the start of the method of FIG. 3, some of the medical images may have already been loaded in accordance with the predetermined loading rules. Others of the medical images have not yet been loaded.

It is known that users may navigate through a set of slices in different ways. In some circumstances, a user may scroll through a set of slice images by making a large scrolling movement. The user may intend to navigate only to an approximate location within the set of slices. The user may expect to arrive at any slice within a desired region of slices, rather than one specific slice.

In other circumstances, a user may want to view every slice. The user may navigate from each slice to a next slice. The user may expect that a navigation action will result in display of a specific slice.

We consider the user as having two modes of operation. One mode of operation may be called localizing. When localizing, the user is not aiming for a specific image. Instead, the user may typically be aiming for a region of interest, for example a particular anatomy. The user makes a user input that is representative of a large scrolling action. For example, the user input may comprise clicking and dragging a mouse. Exactly which image the user will move to when they make a large scrolling action may depend on the performance of the system, and may not be predictable by the user.

The other mode of operation may be called reading. When reading, the user is aiming for a specific image. The user makes a user input that is representative of a small scrolling action. For example, the user input may comprise using the mouse wheel, using a key press, clicking and dragging the mouse by a small amount (less than a threshold amount), or an automatic scroll.

In some circumstances, the user will localize to an approximate area and then once the approximate area will read in this area. In some circumstances, the user will read a study from top to bottom. In reading the study from top to bottom, the user expects to see every slice.

In the embodiment of FIG. 3, the navigation circuitry 28 is configured to distinguish between a large scrolling action and a small scrolling action, and to use a different mode of navigation when receiving a large scrolling action than when receiving a small scrolling action. The navigation circuitry 28 has a different behavior when receiving a user input that is representative of a large scrolling action (localizing) than when receiving a user input that is representative of a small scrolling action (reading).

At stage 50, the navigation circuitry 28 receives data that is representative of a user interaction. The user interaction comprises an input operation, which may also be described as a navigation action. Each input operation is representative of a distance to be moved through the slices from the current location to an updated location.

In the present embodiment, two types of input operation are available to the user. The user may perform a click-and-drag operation to perform a large movement through the slices. The click-and-drag operation may be described as an analogue action. Further examples of an analogue action may include, for example, swiping a touch screen or making a gesture.

Alternatively, the user may use the mouse wheel to perform a small movement through the slices, for example to move by one slice at a time. The movement of the mouse wheel may be described as an atomic action. Other examples of an atomic action may comprise, for example, a keypress or single click.

In other embodiments, any type or types of input operation may be used, which may be analogue and/or atomic.

At stage 52, the navigation circuitry 28 determines whether the input operation is a large scrolling action. The navigation circuitry 28 uses a size of the scrolling action to determine a distance to be travelled. For example, a distance of a click-and-drag operation performed by the user may be translated into a distance along the axis of the body of the subject. A distance by which a mouse wheel is rotated may be translated into a distance along the axis of the body of the subject.

In the present embodiment, the distance to be travelled is expressed as a multiple of the interval between slices. The distance to be travelled may also be referred to as a control amount.

If the control amount is greater than a predetermined threshold distance, the navigation circuitry 28 determines that the input operation is a large scrolling action. The threshold value may be set by default. The threshold value may be set on installation. The threshold value may be selected by a user. In some embodiments, the threshold value may be adjusted dynamically, for example based on system loading.

In other embodiments, any suitable method may be used to determine whether the input operation is of a first type of input operation or a second type of input operation. For example, the navigation circuitry may determine that the input operation is of a first type if the scrolling action is a click-and-drag, and determine that the input operation is of a second type if the scrolling action is a mouse wheel movement. In some embodiments, the determining of the type of the input operation may not depend on a size of the movement, or may only partially depend on the size of the movement.

The navigation circuitry proceeds to stage 54. At stage 54, the navigation circuitry 28 determines an updated location by adding the distance to be travelled to a location of a current image, for example the initial image. The image at the updated location may be referred to as a destination image.

The loading circuitry 24 determines whether the destination image is already loaded. For example, the destination image may be one of the images that has been loaded in accordance with the predetermined loading rule.

If the destination image has already been loaded, the display circuitry 26 displays the destination image. The flowchart ends at stage 62.

If the destination image has not been loaded, the navigation circuitry 28 specifies the closest image of the Nth images.

At stage 56, the navigation circuitry 28 snaps the location to the location of the specified image. If the specified image has already been loaded, the display circuitry 26 displays the specified image on the display screen 16. If the specified image has not yet been loaded, the loading circuitry 24 loads the destination image, and the display circuitry 26 then displays the destination image on the display screen 16.

In the case of a large scrolling action, the user is snapped to the closest one of the Nth images. If the closest of the Nth images has already been loaded, the closest Nth image is displayed instead of the destination image, and the destination image is not loaded on demand. By snapping to the nearest of the Nth images, loading resources are conserved. When considering multiple navigation actions, it may be expected that the number of images loaded will be less than if every images were to be loaded, or if each image to which the user navigated was loaded on demand.

It is expected that when the user makes a large scrolling action, they do not expect to arrive at an exact slice. Therefore, the snapping may not have a negative impact on the user's experience. By making a large scrolling action, the user may indicate that they want to localize in an approximate region of the slices.

In some circumstances, the use of a subset of Nth images may provide a consistent navigational experience to the user. The user may get used to navigating the set of slices in increments of N slices when making large scrolling movements. The user of a regular grid for snapping may mean that the user can form a picture of how the system is behaving. The user may always end up within a consistent distance of a requested location.

In some embodiments, the navigation circuitry 28 always snaps to the nearest of the Nth images when the first type of input operation is used, whether or not the destination image has been loaded. In other embodiments, the navigation circuitry 28 may snap to any suitable image. For example, if the destination image has not yet been loaded, the navigation circuitry 28 may snap to a closest loaded image. The closest loaded image may be, for example, one of the Nth images, one of the closest M images, or an image to which the navigation circuitry 28 has previously navigated.

We turn to the case in which the user interaction is determined not to be a large scrolling action at stage 52. The flowchart proceeds to stage 58. The navigation circuitry 28 determines whether the input operation is a small scrolling action based on the control amount determined at stage 52. If the control amount is below the predetermined threshold value, the navigation circuitry 28 determines that the input operation is a small scrolling action.

The flowchart proceeds to stage 60. The navigation circuitry 28 determines an updated location by adding the distance to be travelled to the current location.

The navigation circuitry 28 moves the location to the updated location, which may also be described as a target location or requested location. If the image at the updated location has not yet been loaded, the loading circuitry 24 loads the image at the updated location. The display circuitry 26 displays the image at the updated location. The flowchart ends at stage 82.

If the action is a small scrolling action, it is assumed that the user is performing a reading operation. Therefore the user wants to move to a particular slice. The user is moved to that slice whether the image for the slice has been loaded or not. No snapping is performed. Instead, the location moves to the updated location, and the image at the updated location is loaded on demand. Loading the image at the current location is the highest priority in loading images.

If the input operation is neither a large scrolling action nor a small scrolling action, the flowchart ends at stage 82 without any navigation being performed.

It is proposed that snapping is acceptable to the user when localizing, but that snapping would not be accepted when reading. Therefore, different navigation behaviors are used when the user is thought to be localizing and when the user is thought to be reading. The navigation when localizing may be somewhat imprecise. The navigation when reading is always precise.

The method of FIGS. 2 and 3 may make efficient use of system resources whilst providing a satisfactory user experience. The method of FIGS. 2 and 3 may be used in enterprise imaging products in which computing resources are shared between multiple users. Parameters (for example, a value of N) may be chosen to trade off providing access to a large number of users versus providing a good user experience.

The method of FIGS. 2 and 3 may use fewer system resources than a method in which all slices are loaded straight away. The system uses fewer system resources by not pre-emptively loading all of the images, but the user may rarely notice the difference between the method of FIGS. 2 and 3 and a method in which all images are loaded pre-emptively.

The method of FIGS. 2 and 3 may provide a better user experience than a method in which each slice is loaded only on request by the user. The user may experience scrolling at a satisfactory rate of frames-per-second. The user may not notice if, when making a large scrolling action, they are snapped to an image that is not exactly the destination image indicated by the size of the scrolling action, but instead is the one of the Nth images that is closest to the destination image.

FIGS. 4 to 7 illustrate examples of loading and of navigation through a set of slices. In the examples shown in FIGS. 4 to 7, N=6.

Figure 4:
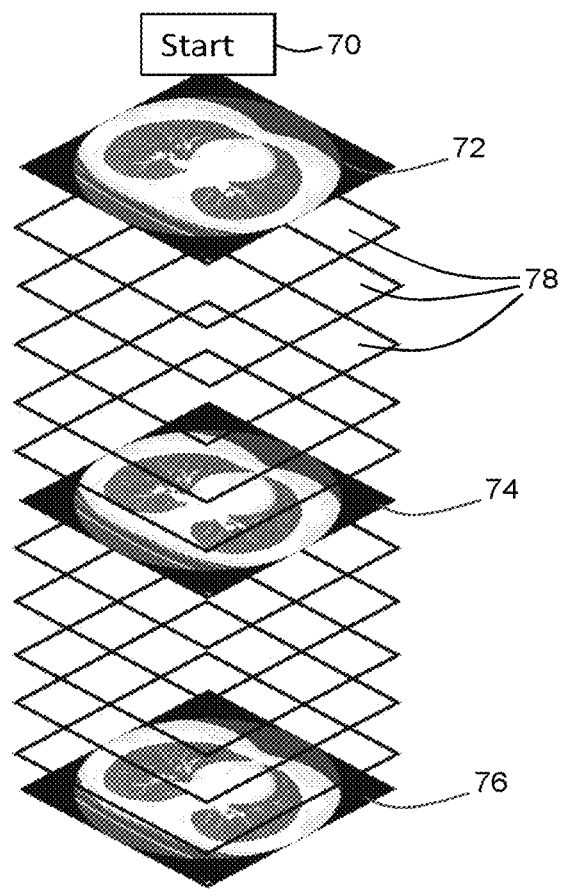
FIG. 4 is a schematic illustration of a set of slices in which every Nth image has been loaded, in accordance with an embodiment.

FIG. 4 represents a set of slices. A start position for loading and navigating the slices is shown by label 70. Slices 72, 74 and 76 have already been loaded and so are represented as images. It may not be the case that these images have yet been displayed to a user. Slices 78 have not yet been loaded and so are shown as blank. The images that have been loaded include an initial image and Nth images. In this example, N is 6.

Figure 5:
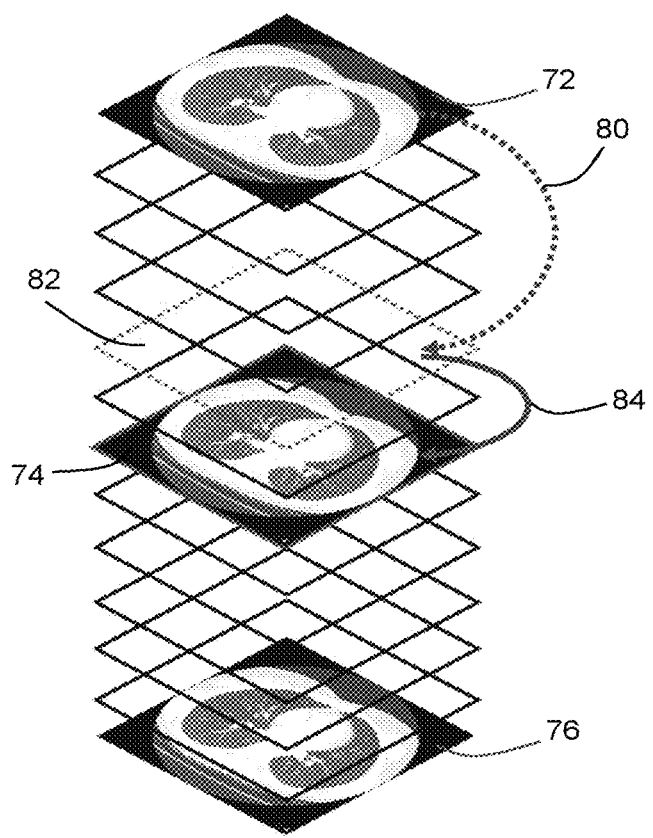
FIG. 5 is a schematic illustration of a set of slices showing navigation by snapping in accordance with an embodiment.

FIG. 5 represents the same set of slices as those in FIG. 4. In the example shown in FIG. 5, a user makes an input operation comprising a large scrolling action. The navigation circuitry 28 determines a distance corresponding to the large scrolling action. The distance is shown by arrow 80. In the example of FIG. 5, the distance of the arrow 80 is four times the increment between slices. In practice, a large scrolling action may often be larger than that shown in FIG. 5. Only a small number of slices are shown in FIG. 5 for simplicity of illustration.

At stage 50 of the method of FIG. 3, the navigation circuitry 28 receives data that represents the input operation. At stage 52, the navigation circuitry 28 determines that the input operation is a large scrolling action. At stage 54, the navigation circuitry 28 determines that the destination image 82 at the end of the arrow 80 has not yet been loaded. The navigation circuitry 28 moves the location to the nearest Nth image, which is image 74 in FIG. 5. The snapping of the location to image 74 is represented by arrow 84. Image 74 has already been loaded. The display circuitry 26 displays image 74.

Figure 6:
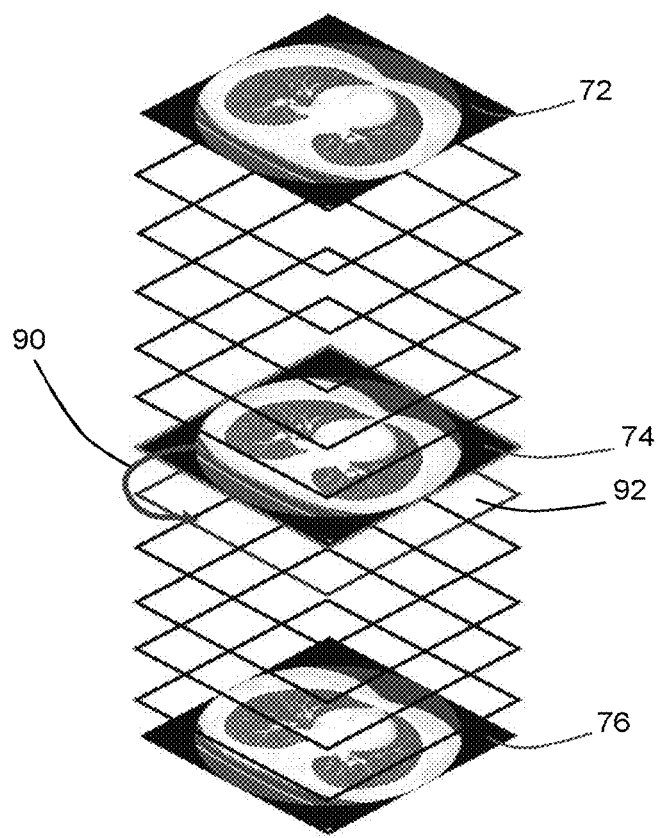
FIG. 6 is a schematic illustration of a set of slices showing navigation in which an image is loaded on demand in accordance with an embodiment.

FIG. 6 represents the same set of slices as those in FIG. 4 and FIG. 5. In the example shown in FIG. 6, the current image is image 74. At stage 50 of FIG. 6, the navigation circuitry 28 receives data representative of an input operation. At stage 58, the navigation circuitry 29 determines that the input operation comprises a small scrolling action. At stage 60, the navigation circuitry 28 determines a distance corresponding to the small scrolling action. The distance is represented by arrow 90 in FIG. 6. The navigation circuitry 28 determines an updated location. In the example of FIG. 6, the destination image at the updated location is image 92. The navigation circuitry 28 moves the current location to the updated location. The loading circuitry 24 loads the destination image 92.

Figure 7:
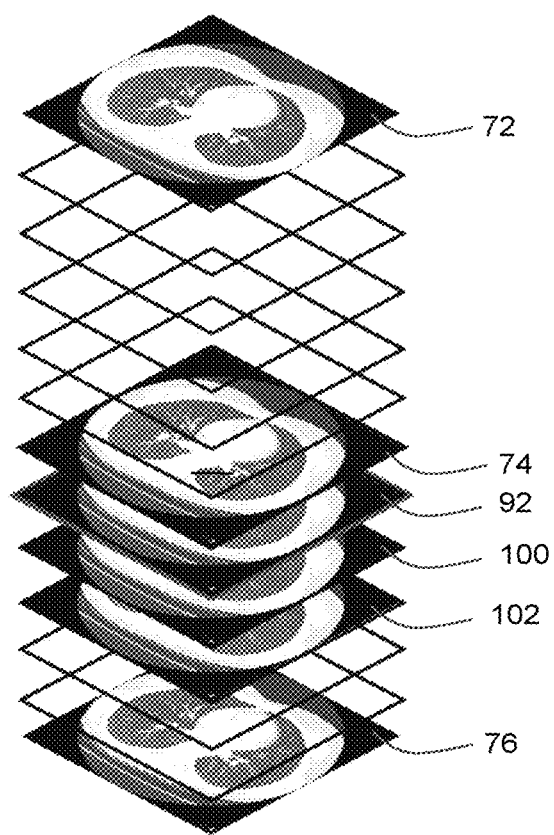
FIG. 7 is a schematic illustration of a set of slices showing loading of slices close to a current image in accordance with an embodiment.

FIG. 7 is representative of loading according to the predetermined loading rule. FIG. 7 represents the same set of slices as those in FIGS. 4, 5 and 6. Slices 72, 74, 76 and 92 have already been loaded. Slice 92 is the current image.

The loading circuitry 24 has already loaded every Nth image. The loading circuitry 24 has already loaded the current image 92. Therefore, according to the predetermined loading rule, loading circuitry 24 loads images 100, 102 which are closest to the current image.

In embodiments described above, a single predetermined loading rule is applied to all navigations through a given set of slices.

In some embodiments, the loading circuitry 24 is configured to switch a loading rule based on a last user action, or last user actions.

In the present embodiment, once every Nth image is loaded, the loading circuitry 24 loads M images around the current position of the user. The loading circuitry 24 loads M images in a negative direction from the current location, and M images in a positive direction from the current location. In other embodiments, the loading circuitry 24 may load images in either a positive or a negative direction (not both). The direction of loading may be based on a direction in which the user was last navigating the slices, for example a direction in which the user was last reading.

In some embodiments, the loading circuitry 24 may switch between loading every Nth image and loading +/− M images around the user location based on whether the last user action was localizing or reading. In one embodiment, the loading circuitry 24 starts by loading every Nth image. If a localizing action is performed by the user, the loading circuitry 24 continues to load every Nth image. If a reading action is performed by the user, the loading circuitry 24 switches to loading images around the user location, even if there are some of the Nth images that have not yet loaded. If the user then performs a localizing action, the loading action 24 switches back to loading every Nth image. In other embodiments, any loading rules may be used.

In the present embodiment, the predetermined loading rule comprises loading every Nth image in increasing order, starting with the first image. In other embodiments, any suitable order of loading the Nth images may be used. The order of loading the Nth images may be changed in response to a user action. The order may be changed to prioritize loading the Nth images nearest to a current location. A direction in which the Nth images are loaded (positive or negative) may be selected in dependence on a direction of navigation by the user.

The loading circuitry 24 may load only some of the Nth images. For example, the loading circuitry 24 may only load the X images of the Nth images that are closest to a current location. The loading of only the Nth images that are closest to the current location may be based on an assumption that the user can only move the scroll location at a certain maximum rate.

In some embodiments, the loading rule may prioritize loading images around a location of interest, for example a finding or anatomical landmark. In some embodiments, the loading circuitry 24 loads every image around a location of interest. In some embodiments, the loading circuitry 24 decreases the value of N around a location of interest, thereby loading a denser grid of images around the location of interest than in the rest of the series of images.

In some embodiments, the loading rule may first load thick slices, and then subsequently load thin slices.

Loading rules may be tuned on installation. Values of N, M, X or other parameters may be selected manually or automatically. A threshold value of distance that distinguishes large scrolling actions from small scrolling actions may be selected manually or automatically. In some circumstances, values of parameters may be changed dynamically based on a current load on the system.

In some embodiments, a model is trained to classify an action as a localizing action or a reading action. The classification of localizing versus reading may then be used by the navigation circuitry 28 to determine whether or not to snap to a nearest loaded image.

In some embodiments, a model is trained to predict a user's next action in dependence on the user's previous actions. As a simple example, if a user has made multiple reading actions in one direction, the model may predict a further reading action in the same directions. In some circumstances, the model may make more complex predictions. For example, the model may predict how a user may alternate localizing and reading. The trained model may comprise, for example, a long short-term memory (LSTM). In some embodiments, the model is trained on the actions of a large cohort of users. In some embodiments, the model is trained on the actions of a single user, such that the model is tailored to the actions of that user. Different users may have different patterns of browsing.

The model's prediction of the user's next action may be used as an input to a loading rule. The selection of which image to load next may be based on the prediction of the user's next action.

In embodiments described below, each of the images of the series of images is representative of a respective, different location in space. Each of the images is representative of a position along a subject's body. In other embodiments, the locations may be spatial locations which are not locations along a subject's body.

In further embodiments, each of the images of the series may be representative of a respective, different location in time. For example, the images may form a time series of images. The images may be representative of different phases of motion (for example, heart motion or breathing motion). The images may be representative of different stages in the introduction of contrast, or different stages of perfusion.

Certain images provide a medical imaging storage apparatus comprising a series of images relevant to the user; an image loading operation with significant resource cost; ability to view a specified image in the series; a navigation action performed by the user that modifies which image to view; in which: the system prioritizes loading the image for the current location; the system then prioritizes loading the next unloaded image from a set of image locations; the system finally prioritizes loading images around the current location; the system determines if the navigation action performed by the user is for localizing or reading; the system updates the viewing location based on: the user action, the determination of whether the user action is classed as localizing or reading, the set of candidate image locations, and the loaded/unloaded state of images.

The system may determine if an action is a localizing action or reading action by assessing the user's intended change in location over time and the mechanism by which the user changes the location. The user may perform an atomic action such as a keypress. The atomic action may be determined as a reading action. The user may perform an analogue action, such as a mouse dragging operation, which moves a small amount of a longer period of time. The analogue action may be determined as a reading action. The user may perform an analogue action, such as a mouse dragging operation, which moves a larger amount in a shorter period of time. The analogue action may be determined as localizing action.

The system may respond to a localizing action by moving to the target location if the target location is loaded, and otherwise by snapping to the nearest location in the set of candidate locations. The system may respond to reading action by always moving to that location.

The set of candidate locations may be every Nth image as regularly spatially distributed throughout the series. This value may be adjusted.

Certain embodiments provide a method of loading and displaying medical images from a stored set of medical images, each medical image corresponding to a respective different location, comprising: determining an image viewing location; selecting a subset of the images based on the determined image viewing location, each image of the subset corresponding to a respective different location at or in a range around the image viewing location, wherein locations of non-selected images of the set are interspersed with the locations of the selected images of the subset such that the subset represents the range of locations with fewer images than the set of images; performing a loading operation to load the selected images; and receiving a navigation action that navigates to an updated image viewing location and performing either a first image display process if the navigation action is of the first type or a second image display process if the navigation action is of a second type, wherein the first, less location-accurate image display process comprises selecting an already-loaded one of the subset of images that is closest to the updated image viewing location, even if it is further from the updated image viewing location than non-loaded images of the set, and displaying that selected image; the second, more location-accurate image display process comprises performing a further loading operation to load a further image from the set of images if that further image corresponds more closely to the updated image viewing location than images of the loaded subset, and displaying that further image.

The first type of navigation action may comprise a navigation action determined to be a coarse or localization action, for example scanning or searching the range, and the second type of navigation action is determined to be a reading action that is taken as indicating that a user wishes to view a specific image for the updated imaging location.

The type of navigation action may be determined in dependence on a difference between the image viewing location and the updated image viewing location, wherein: the first image display process comprises, if the difference between the image viewing location and the updated image viewing location is greater than a threshold amount, selecting one of the subset of selected images that is closest to the updated image viewing location and displaying that selected image; the second image display process comprises, if the difference between the image viewing location and the updated image viewing location is less than or equal to a threshold amount, performing a further loading operation to load a further image from the set of images that corresponds more closely to the updated image viewing location than images of the subset and displaying that further image.

The type of navigation action may be determined based on at least one of a rate of change of image viewing location represented by the navigation action, or a type or property of user input that is used to produce the navigation action (for example, an atomic action such as a keypress, or an analogue action such as a mouse dragging operation).

The locations may be physical locations and the range may be a range in physical space. The locations may be locations in time. The range may be a time range. The set of medical images may represent a time series.

The loading operation may comprise loading the selected images of the subset in the determined order. The order may be determined based on distance from the determined image viewing location.

The order may comprise: firstly loading the image at or closest to the image viewing location; secondly loading other images of the subset; thirdly loading further images closest to the image viewing location that are not included in the subset.

The method may comprise halting the loading operation, if not yet completed, in response to the navigation action and then starting a further selecting and loading operation for a further subset determined based on the updated image viewing location.

Certain embodiments comprise a medical system comprising: processing circuitry configured to: acquire medical image data sequentially from a memory which stores a plurality of slice medical image data, based on a predetermined data acquiring rule, receive an input operation to display the medical image data on a display, display the medical image data based on the input operation, receive, slice positional information of medical image data which is displayed on the display and control amount relating to update of slice position of the medical image data which is displayed on the display, as the input operation, specify a displaying medical image data which has already finished acquiring from the memory, among a plurality of slice medical image data including a display target based on the received slice positional information, when the control amount corresponds to an amount larger than a predetermined threshold and the medical image data corresponds to the slice position of the display target has not finished acquiring from the memory, display the specified displaying medical image data on the display.

The processing circuitry may be further configured to acquire a displaying medical image data corresponds to the slice position of the display target from the memory based on the received slice positional information, when the control amount corresponds to an amount smaller than a predetermined threshold and the medical image data corresponds to the slice position of the display target has not finished acquiring from the memory, display the specified displaying medical image data on the display.

The predetermined data acquiring rule may be to acquire the medical image data of the first slice position and acquire the medical image data of a second slice position which is not adjacent to the first slice position after acquiring the medical image data of the first slice.

Certain embodiments comprise a medical system comprising: processing circuitry configured to: acquire medical image data sequentially from a memory which stores a plurality of slice medical image data, based on a predetermined data acquiring rule, receive an input operation to display the medical image data on a display, display the medical image data based on the input operation, receive, slice positional information of medical image data which is displayed on the display and control amount relating to update of slice position of the medical image data which is displayed on the display, as the input operation, acquire a displaying medical image data corresponds to the slice position of the display target from the memory based on the received slice positional information, when the control amount corresponds to an amount smaller than a predetermined threshold and the medical image data corresponds to the slice position of the display target has not finished acquiring from the memory, display the specified displaying medical image data on the display.

The processing circuitry may be further configured to specify a displaying medical image data which has already finished acquiring from the memory, among a plurality of slice medical image data including a display target based on the received slice positional information, when the control amount corresponds to an amount larger than a predetermined threshold and the medical image data corresponds to the slice position of the display target has not finished acquiring from the memory, display the specified displaying medical image data on the display.

The predetermined data acquiring rule may be to acquire the medical image data of the first slice position and acquire the medical image data of a second slice position which is not adjacent to the first slice position after acquiring the medical image data of the first slice.

Whilst particular circuitries have been described herein, in alternative embodiments functionality of one or more of these circuitries can be provided by a single processing resource or other component, or functionality provided by a single circuitry can be provided by two or more processing resources or other components in combination. Reference to a single circuitry encompasses multiple components providing the functionality of that circuitry, whether or not such components are remote from one another, and reference to multiple circuitries encompasses a single component providing the functionality of those circuitries.

Whilst certain embodiments have been described, these embodiments have been presented by way of example only, and are not intended to limit the scope of the invention. Indeed the novel methods and systems described herein may be embodied in a variety of other forms. Furthermore, various omissions, substitutions and changes in the form of the methods and systems described herein may be made without departing from the spirit of the invention. The accompanying claims and their equivalents are intended to cover such forms and modifications as would fall within the scope of the invention.

The invention claimed is:

1. A medical system comprising:
processing circuitry configured to:
 load medical images sequentially from a data store which stores a set of medical images, each of the medical images having an associated location;
 receive a current location of a medical image that is currently displayed on a display;
 receive an input operation from a user;
 process the input operation to determine whether the input operation is of a first type or the input operation is of a second type, wherein the first type of input operation is less precise than the second type of input operation, and determine a destination location in dependence on the current location and the input operation, and wherein processing of the input operation to determine whether the input operation is of the first type or the input operation is of the second type comprises processing the input operation to obtain a control amount representative of an update to the current location, determining that the input operation is of the first type if the control amount is larger than a predetermined threshold, and determining that the input operation is of the second type if the control amount is not larger than the predetermined threshold;
 perform a first display operation based on the destination location if the input operation is of the first type; and
 perform a second display operation based on the destination location if the input operation is of the second type.

2. The medical system of claim 1, wherein the first type of input operation comprises a first type of navigation action and the second type of input operation comprises a second type of navigation action, the first type of navigation action comprising a localization action and the second type of navigation action comprising a reading action.

3. The medical system of claim 1, wherein loading of the medical images is in accordance with a predetermined data loading rule that specifies loading a selected subset of the medical images before others of the medical images.

4. The medical system of claim 3, wherein the first display operation comprises:
 determining whether the medical image at the destination location has yet been loaded from the data store;
 if the medical image at the destination location has been loaded, displaying on the display the medical image at the destination location; and
 if the medical image at the destination location has not yet been loaded:
  specifying a closest medical image of the selected subset of the medical images, wherein the closest medical image is the medical image of the selected subset that has a location that is closest to the destination location;
  loading the closest medical image if the closest medical image has not yet been loaded; and
  displaying on the display the closest medical image.

5. The medical system of claim 3, wherein the first display operation comprises:
 specifying a closest medical image of the selected subset of the medical images, wherein the closest medical image is the medical image of the selected subset that has a location that is closest to the destination location;
 loading the closest medical image if the closest medical image has not yet been loaded; and
 displaying on the display the closest medical image.

6. The medical system of claim 1, wherein the second display operation comprises:
 loading the medical image associated with the destination location if the medical image associated with the destination location has not yet been loaded; and
 displaying on the display the medical image associated with the destination location.

7. The medical system of claim 1, wherein the loading of the medical images sequentially from the data store is in accordance with a predetermined data loading rule comprising loading the medical images in an order such that loading of a first medical image is followed by loading of a second medical image that is not adjacent to the first medical image in location.

8. The medical system of claim 1, wherein the loading of the medical images sequentially from the data store is in accordance with a predetermined loading rule comprising loading medical images based on distance from the location of the medical image that is currently displayed and/or based on distance from the updated location.

9. The medical system of claim 1, wherein the loading of the medical images sequentially from the data store is in accordance with a predetermined loading rule comprises:
 firstly loading a medical image at or closest to the current location;
 secondly loading medical images of a subset of images, the subset representing a range of locations of the medical images using fewer images than all of the medical images; and
 thirdly loading medical images closest to the location of the medical image that is currently displayed.

10. The medical system of claim 1, wherein the loading of the medical images sequentially from the data store is in accordance with a predetermined loading rule comprises loading at least one medical image having a location corresponding to at least one of: a region of interest, a finding, an anatomical landmark.

11. The medical system of claim 1, wherein the locations are physical locations and a range of the locations is a range in physical space.

12. The medical system of claim 1, wherein the locations are locations along a body of a subject, and the medical images are slice medical images.

13. The medical system of claim 1, wherein the locations are locations in time, a range of the locations is a range in time, and the medical images are representative of a time series.

14. The medical system of claim 3, wherein the predetermined data loading rule comprises a trained model.

15. The medical system of claim 3, wherein the processing circuitry is configured to apply a trained model to predict a next input operation from the user, and to modify the predetermined data loading rule in dependence on the predicted next input operation.

16. A medical system, comprising:
 processing circuitry configured to:
  load medical images sequentially from a data store which stores a set of medical images, each of the set of medical images having an associated location;
  receive a current location of a medical image that is currently displayed on a display;
  receive an input operation from a user;
  process the input operation to determine whether the input operation is of a first type or the input operation is of a second type, wherein the first type of input operation is less precise than the second type of input operation, and determine a destination location in dependence on the current location and the input operation;
  perform a first display operation based on the destination location if the input operation is of the first type, wherein the first display operation comprises, if the destination location corresponds to a medical image that has not yet been loaded from the data store, specifying a medical image of the set of medical images that has been loaded from the data store, and displaying on the display the specified medical image; and
  perform a second display operation based on the destination location if the input operation is of the second type.

17. The medical system of claim 16, wherein the specified medical image is a closest one of the medical images to the destination location that has already been loaded.

18. A method comprising:
 loading medical images sequentially from a data store which stores a set of medical images, each of the medical images having an associated location;
 receiving a current location of a medical image that is currently displayed on a display;
 receiving an input operation from a user;
 processing the input operation to determine whether the input operation is of a first type or the input operation is of a second type, wherein the first type of input operation is less precise than the second type of input operation, and determining a destination location in dependence on the current location and the input operation, and wherein the processing of the input operation to determine whether the input operation is of the first type or the input operation is of the second type comprises processing the input operation to obtain a control amount representative of an update to the current location, determining that the input operation is of the first type if the control amount is larger than a predetermined threshold, and determining that the input operation is of the second type if the control amount is not larger than the predetermined threshold;

performing a first display operation based on the destination location if the input operation is of the first type; and performing a second display operation based on the destination location if the input operation is of the second type.

\* \* \* \* \*